United States Patent [19]

Koike et al.

[11] Patent Number: 5,305,650
[45] Date of Patent: Apr. 26, 1994

[54] AUTOMATIC PREPARATION APPARATUS

[75] Inventors: Toshio Koike; Toshiyuki Mochizuki; Keiko Gondo, all of Kawasaki, Japan

[73] Assignee: Ajinomoto Co., Inc., Tokyo, Japan

[21] Appl. No.: 782,108

[22] Filed: Oct. 24, 1991

[30] Foreign Application Priority Data

Oct. 29, 1990 [JP] Japan ................. 2-291323

[51] Int. Cl.⁵ ............................................. G01N 35/06
[52] U.S. Cl. ................................................. 73/864.21
[58] Field of Search ............... 73/863, 863.01, 864.16, 73/864.21-864.25, 863.11, 864.26; 422/100, 63-65, 70, 74

[56] References Cited

U.S. PATENT DOCUMENTS

| | | | |
|---|---|---|---|
| 3,607,099 | 9/1971 | Scordato et al. | 23/259 |
| 4,170,625 | 10/1979 | Welch . | |
| 4,413,534 | 11/1983 | Tomoff et al. | 73/864.21 |
| 4,497,774 | 2/1985 | Scordato | 422/73 |
| 4,554,132 | 11/1985 | Collins | 422/74 |
| 4,836,038 | 6/1989 | Baldwyn | 73/864.21 |
| 4,855,909 | 8/1989 | Vincent et al. | 622/64 |
| 4,970,468 | 11/1990 | Ishizawa et al. | 73/864.24 |
| 4,974,458 | 12/1990 | Koike . | |
| 5,167,926 | 12/1992 | Kimura | 422/67 |

FOREIGN PATENT DOCUMENTS 62-44222  9/1987  Japan .

Primary Examiner—Robert Raevis
Attorney, Agent, or Firm—Oblon, Spivak, McClelland, Maier & Neustadt

[57] ABSTRACT

An automatic preparation apparatus comprising turntable means for mounting thereon a plurality of containers including sample containers, rack means, provided at a stationary position separate from the turntable means, for mounting thereon a plurality of sample containers, robot means for transferring the sample containers between the turntable means and the rack means, and control means for performing desired treatments on the liquid in the sample containers on the turntable means.

9 Claims, 20 Drawing Sheets

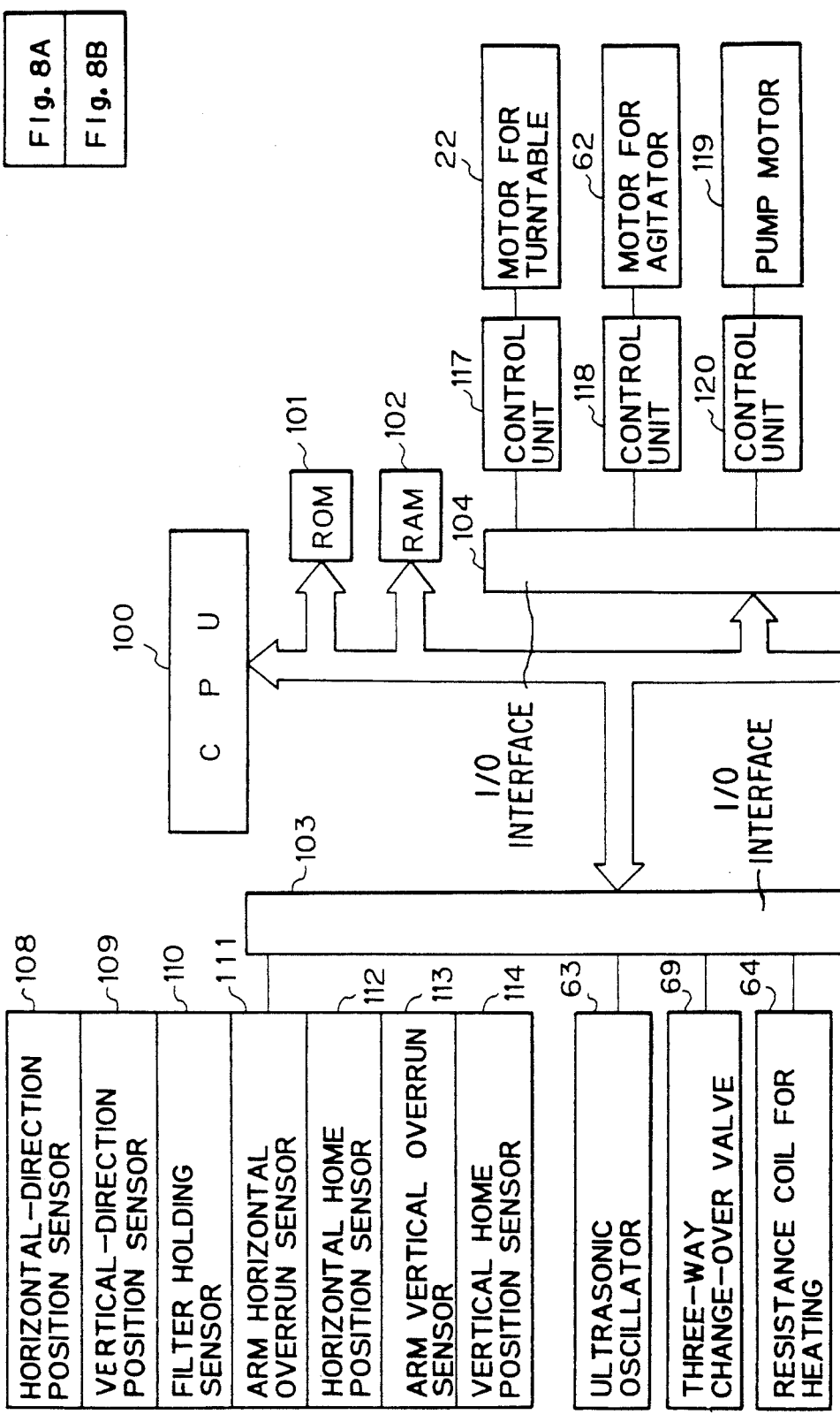

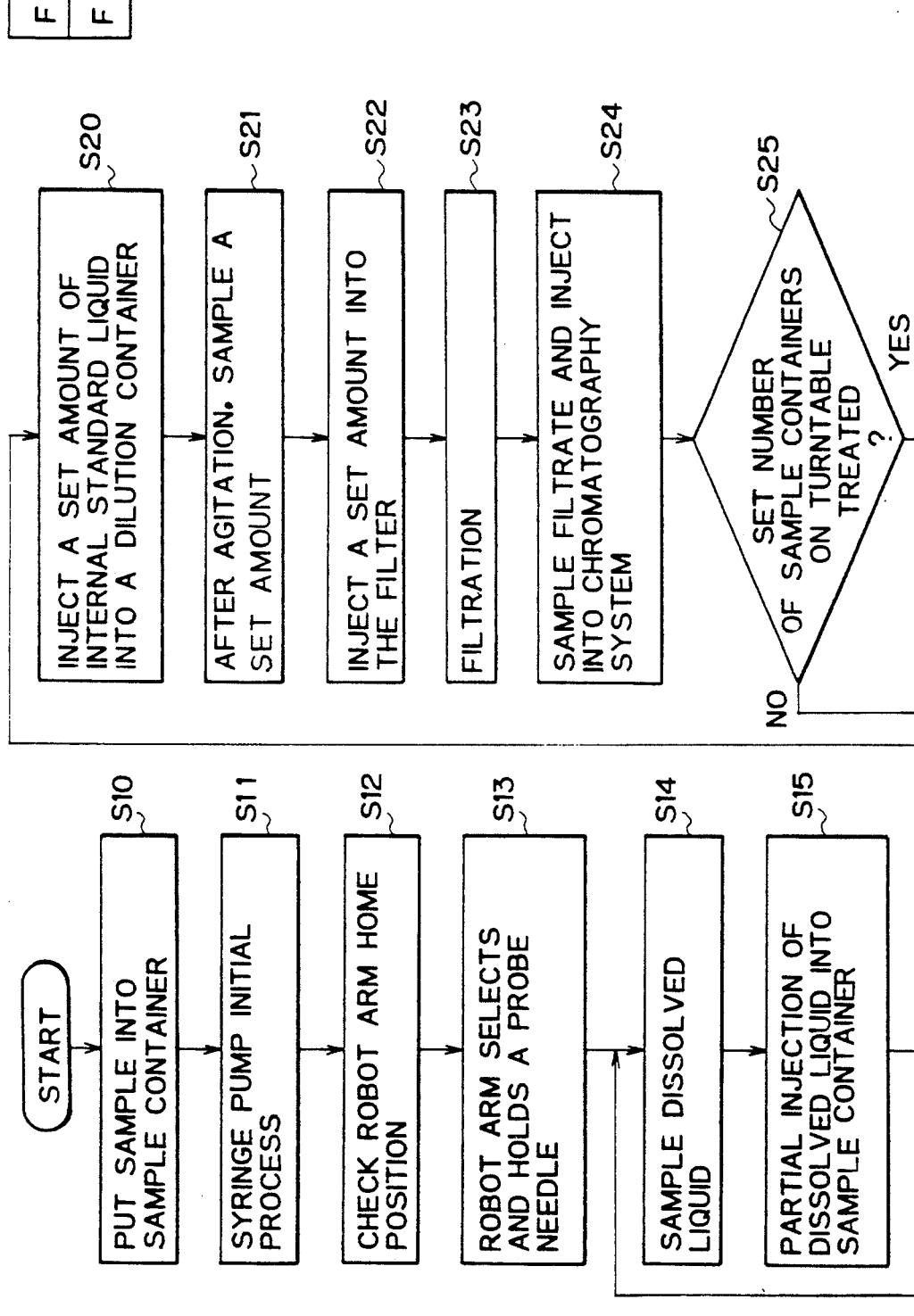

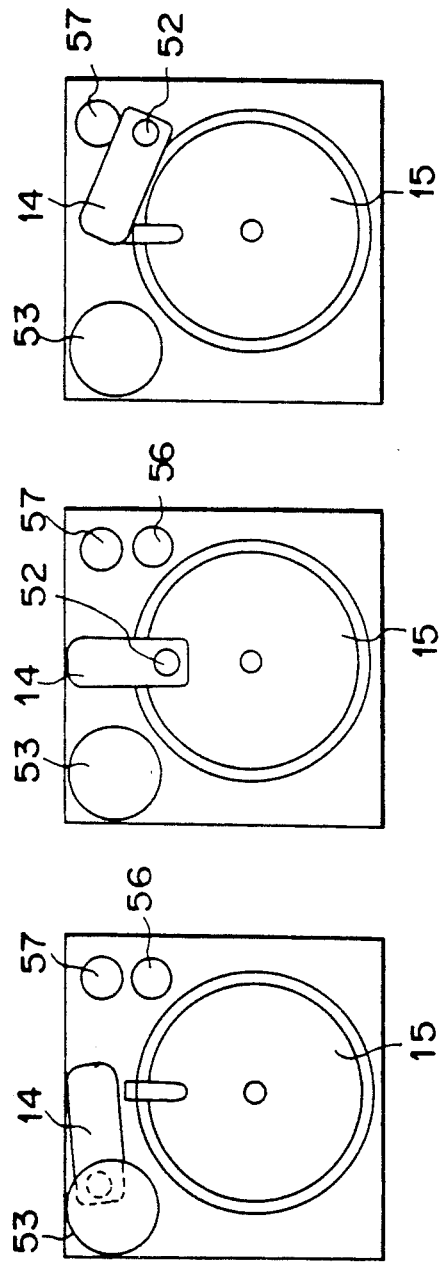
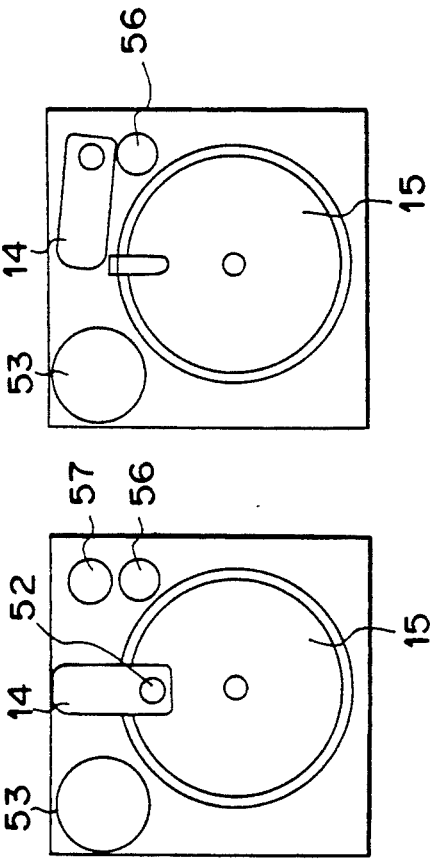

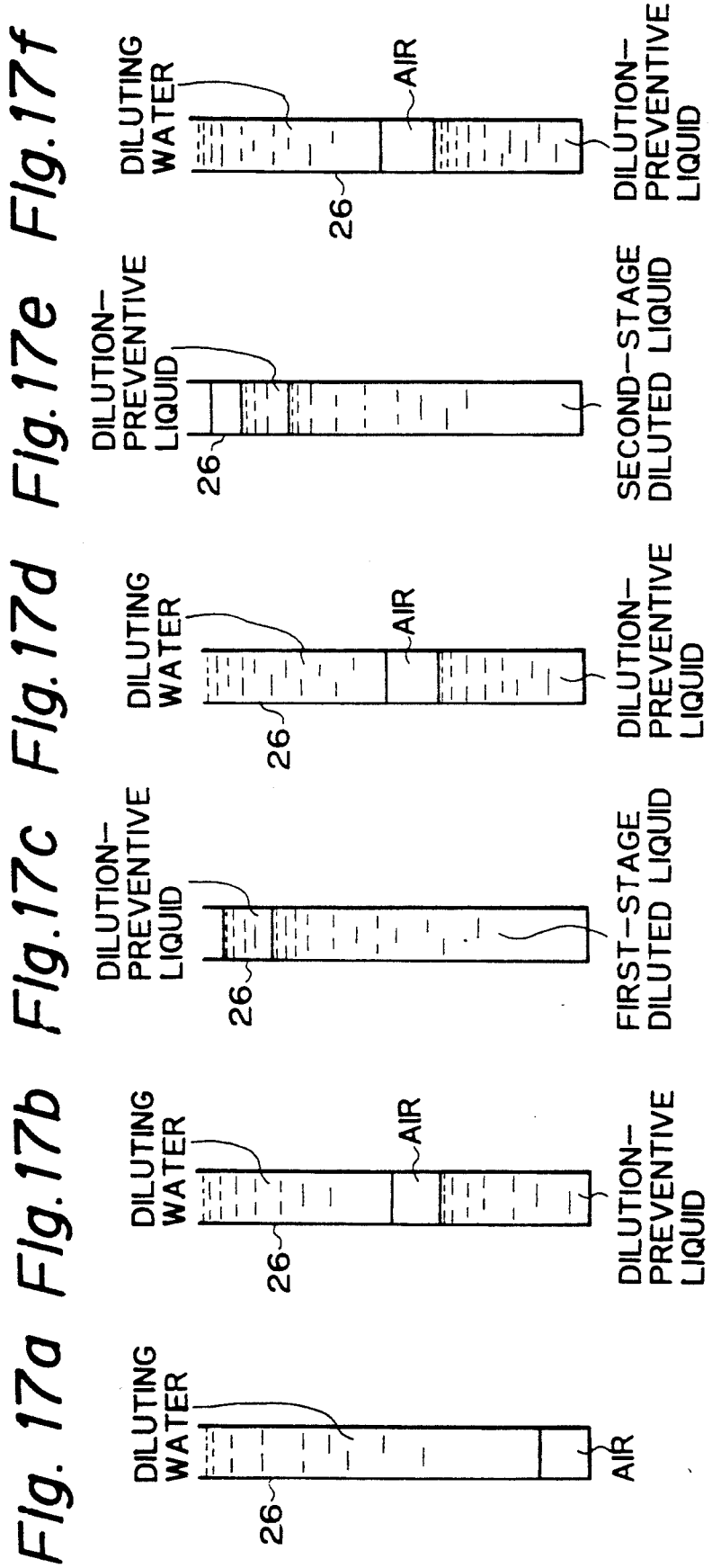

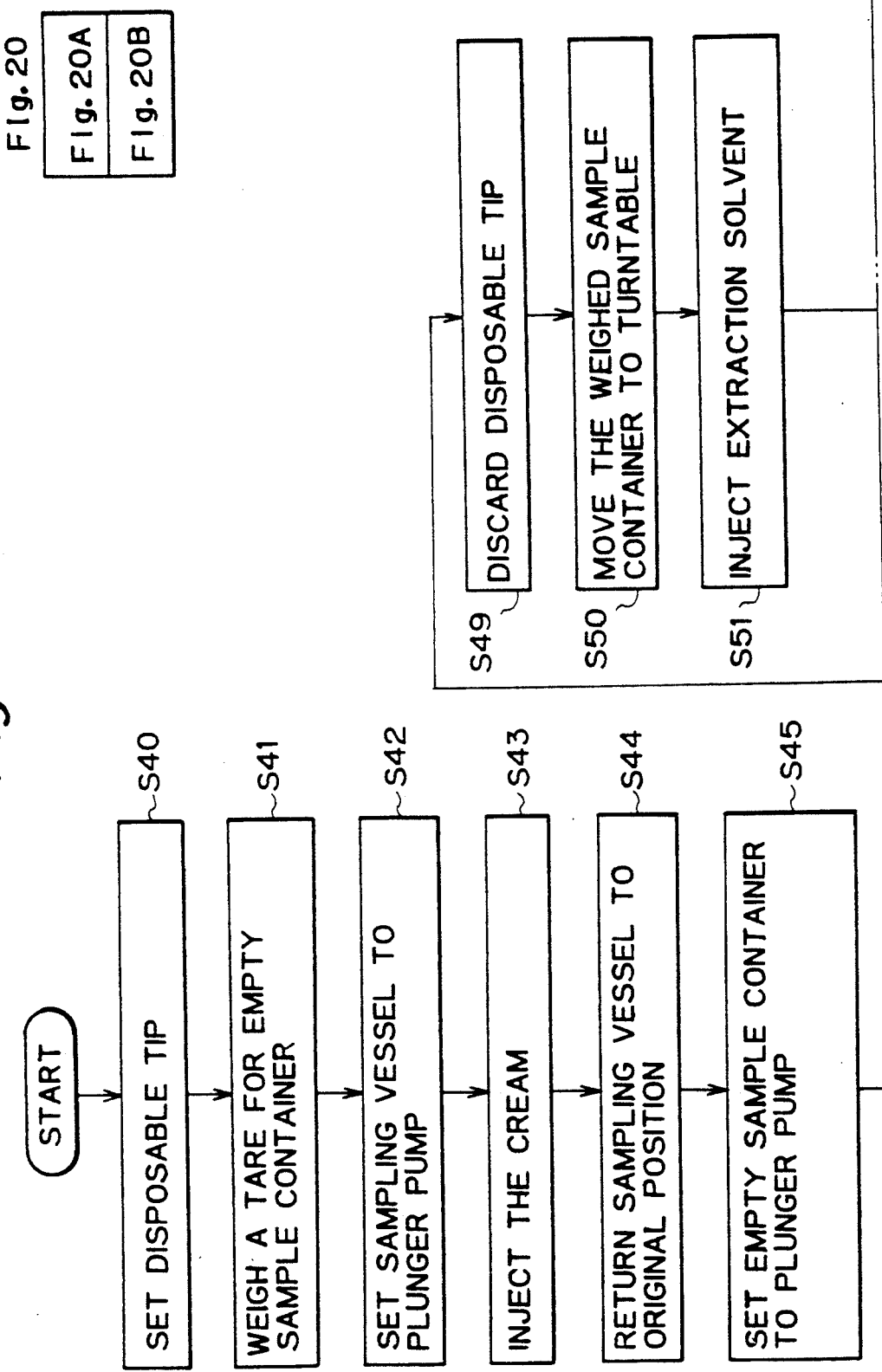

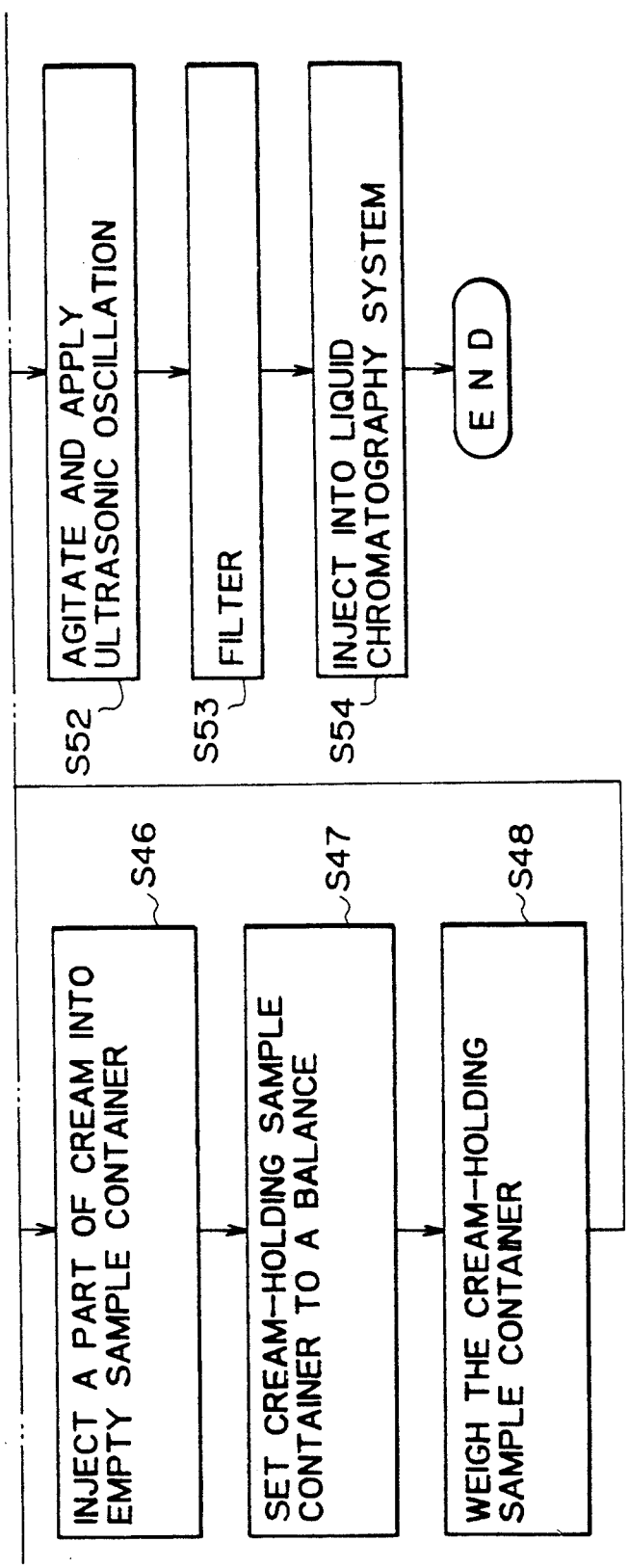

AUTOMATIC PREPARATION APPARATUS

BACKGROUND OF THE INVENTION

1. Field of the Invention

The present invention relates to an automatic preparation apparatus for automatically performing preparation steps such as dissolution, extraction, filtration, dilution and reaction with reagent of a sample liquid.

2. Description of the Related Art

When a sample is injected into a component analysis system for component analysis, suspended matter contained in the sample is usually removed previously to dilute it to a predetermined concentration.

A centrifugal separator or a disposable filter is used for removing the suspended matter from the sample, while a measuring pipette is used for diluting the sample.

For example, when a liquid chromatography system is used for component analysis, neither of the above-mentioned means for removing and diluting the suspended matter can directly be coupled with the liquid chromatography system for operational reasons and thus the prepared sample is set to an automatic sampler or supplied to an injector by means of a microsyringe. Consequently, the liquid chromatography system cannot be operated fully automatically from preparation to analysis of the sample, and the preparation steps of the sample are currently being carried out manually.

However, if the preparation is carried out manually, there are disadvantages including a vast amount of treatment time required, as well as the possible occurrence of treatment error and contamination of the sample. Another disadvantage is that the preparation and component analysis by the liquid chromatography system cannot automatically be controlled in an interlocked manner.

To solve those disadvantages, the present applicant has proposed an automatic preparation apparatus which can mount a plurality of test tubes radially on a turntable, uses a filter robot for moving a detachable filter to above one of those test tubes and a probe robot for sampling a predetermined amount of a liquid from each test tube and injecting a predetermined amount of a liquid into each test tube and filter, and which can perform a desired preparation process by controlling the turntable, filter robot and probe robot in accordance with a predetermined sequence (U.S. Pat. No. 4,951,513).

However, according to the above-mentioned automatic preparation apparatus, the number and capacity of test tubes mountable on the turntable is limited, so that it is difficult to perform automatic preparation using a necessary number of large-capacity sample containers. If the area of the turntable is increased, the number and the capacity of containers can be increased, which, however, results in a considerable increase in the size of the whole apparatus, so that such a large apparatus is inconvenient for installation in laboratories or the like.

SUMMARY OF THE INVENTION

It is therefore an object of the present invention to provide an automatic preparation apparatus that allows a necessary number of large-capacity sample containers to be used and which can be set up in a compact configuration.

According to the present invention, there is provided an automatic preparation apparatus comprising turntable means for mounting a plurality of containers including sample containers, rack means, disposed in a stationary position separate from the turntable means, for mounting a plurality of sample containers, robot means for transferring the sample containers between the turntable means and the rack means, and control means for performing a desired treatment of the liquid in the sample containers on the turntable means.

The robot means transfers a sample container from the rack means to the turntable means, and after treatment for the sample container is finished, the sample container is returned automatically from the turntable means to the rack means. Therefore, only necessary sample containers are mounted on the turntable means, which makes it possible to use large-capacity sample containers without increasing the area of the turntable. In other words, a necessary number of large-capacity sample containers can be used and the whole apparatus can be set in a compact form.

The automatic preparation apparatus preferably further comprises probe means for sampling a predetermined amount of the liquid contained in the containers on the turntable means and that the robot means can move the probe means to a desired position.

The robot means preferably can selectively change over the use of an attachment for holding the probe means and an attachment for holding a sample container.

The robot filter means is preferably further provided which can move a detachable filter to above one of the containers on the turntable means and that the probe means can inject a predetermined amount of liquid into the filter.

The filter robot means is arranged so that a filter is supplied from above the filter robot means and discarded downwardly.

Preferably, the automatic preparation apparatus further comprises a filter supply unit for supplying unused filters of multiple kinds and the robot means can select one of the multiple kinds of filters.

The automatic preparation apparatus may be arranged to perform filtration with multiple stages of filters.

Preferably, the control means comprises a microcomputer in which a sequence of desired treatments is programmed and the drive of the turntable means, robot means, probe means and filter robot means is controlled according to instructions from the microcomputer.

The probe means preferably comprises a probe needle the tip of which can be inserted into each container, and a microsyringe pump for sucking and discharging a predetermined amount of the liquid through the probe needle.

Preferably, the automatic preparation apparatus is provided with multiple kinds of probe needles and the robot means can select one of the multiple kinds of probe needles.

A liquid chromatography system may be arranged such that an input port is provided at a fixed position and the tip of the probe needle can be inserted into the input port.

The automatic preparation apparatus may further comprise plunger means for sampling a creamy substance, and weighing means for weighing the creamy substance sampled with the plunger means.

It is preferable that the turntable means comprises a heating block for heating each container and a cooling block for cooling each container, and that these blocks are partitioned.

The filter robot means preferably is provided with a support member and an arm member which is mounted on the upper portion of the post member and extends horizontally, and the arm member has a filter holding means for releasably holding the filter. The support post member is preferably provided with drive means which allows the arm member to be turned in a horizontal plane so that the exit end of the filter can be located right above one of the containers.

Preferably, the arm member is provided with a sealing mechanism for sealing the injection side of the filter and a mechanism for feeding the pressurized gas into the injection side while the injection side is sealed.

Preferably, the automatic preparation apparatus is provided with a discard port into which the used filters are thrown down in addition to the filter supply unit for supplying unused filters while the drive means of the support post member is so arranged that it may turn the arm member so that the filter holding mechanism may be positioned right below the filter supply unit or right above a discard box.

The arm member is pivotally supported on the support post member in such a way that it may turn in a vertical plane, and may be provided with drive means for turning the arm member for a predetermined angle in the vertical plane.

Preferably, cleaning means is provided at a fixed position for cleaning the robe needle and the microsyringe pump while the tip of the probe needle can be inserted into the cleaning mechanism.

Further objects and advantages of the present invention will be apparent from the following description of the preferred embodiments of the invention as illustrated in the accompanying drawings.

BRIEF DESCRIPTION OF THE DRAWINGS

FIGS. 16a to 16e are views for explaining the operation of the probe means, robot means and filter robot means in the mode of FIG. 15;

FIGS. 17a to 17f are views showing the behavior of the liquid in the probe needle;

FIG. 20 composed of FIGS. 20A and 20B is a flowchart showing the flow in the mode of treatment of a creamy sample.

DESCRIPTION OF THE PREFERRED EMBODIMENTS

The automatic preparation apparatus according to the present invention will be described in detail with reference to the accompanying drawings.

Figure 1:
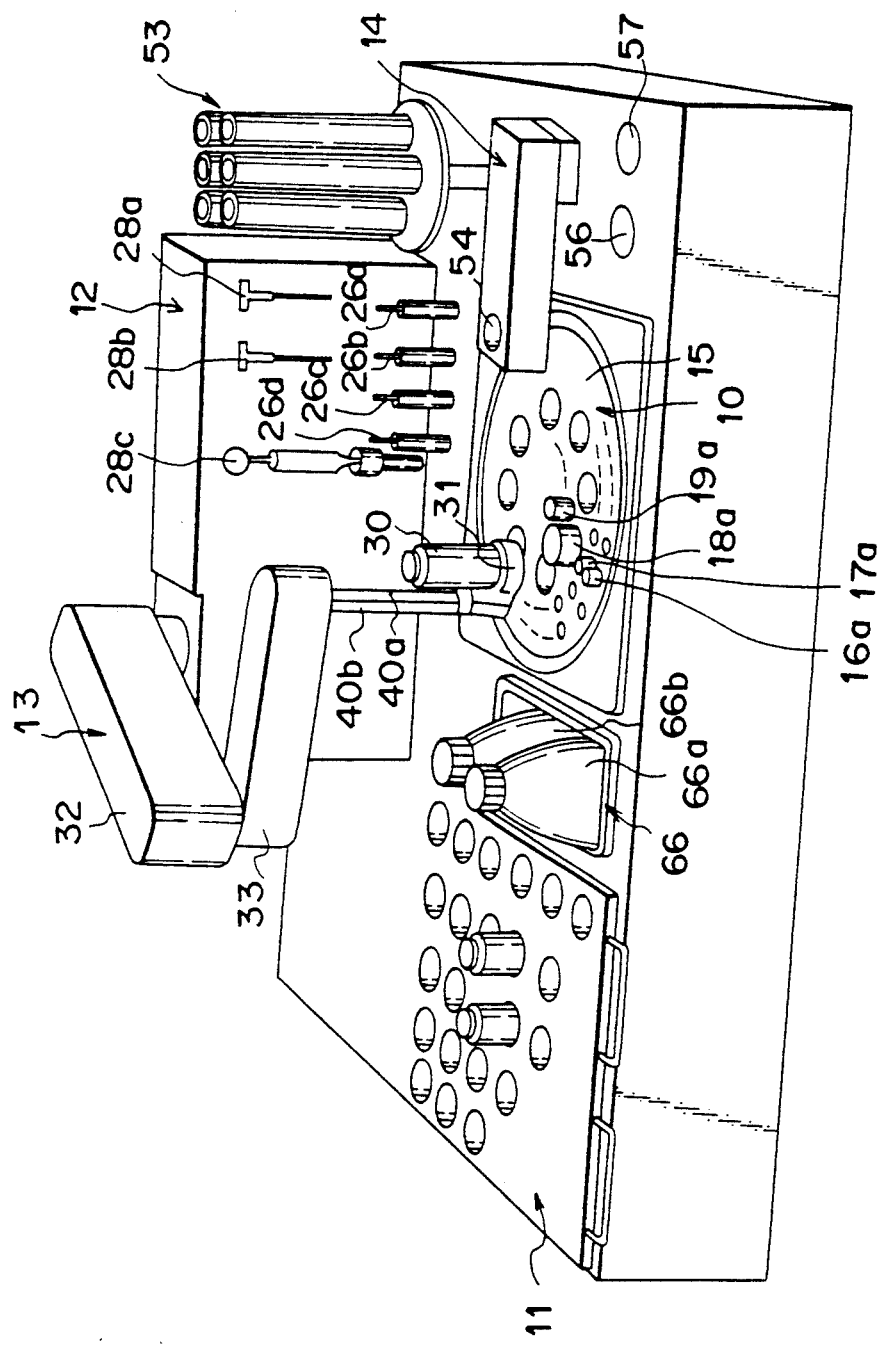
FIG. 1 is a schematic representation of the arrangement of one preferred embodiment according to the present invention.
Figure 2:
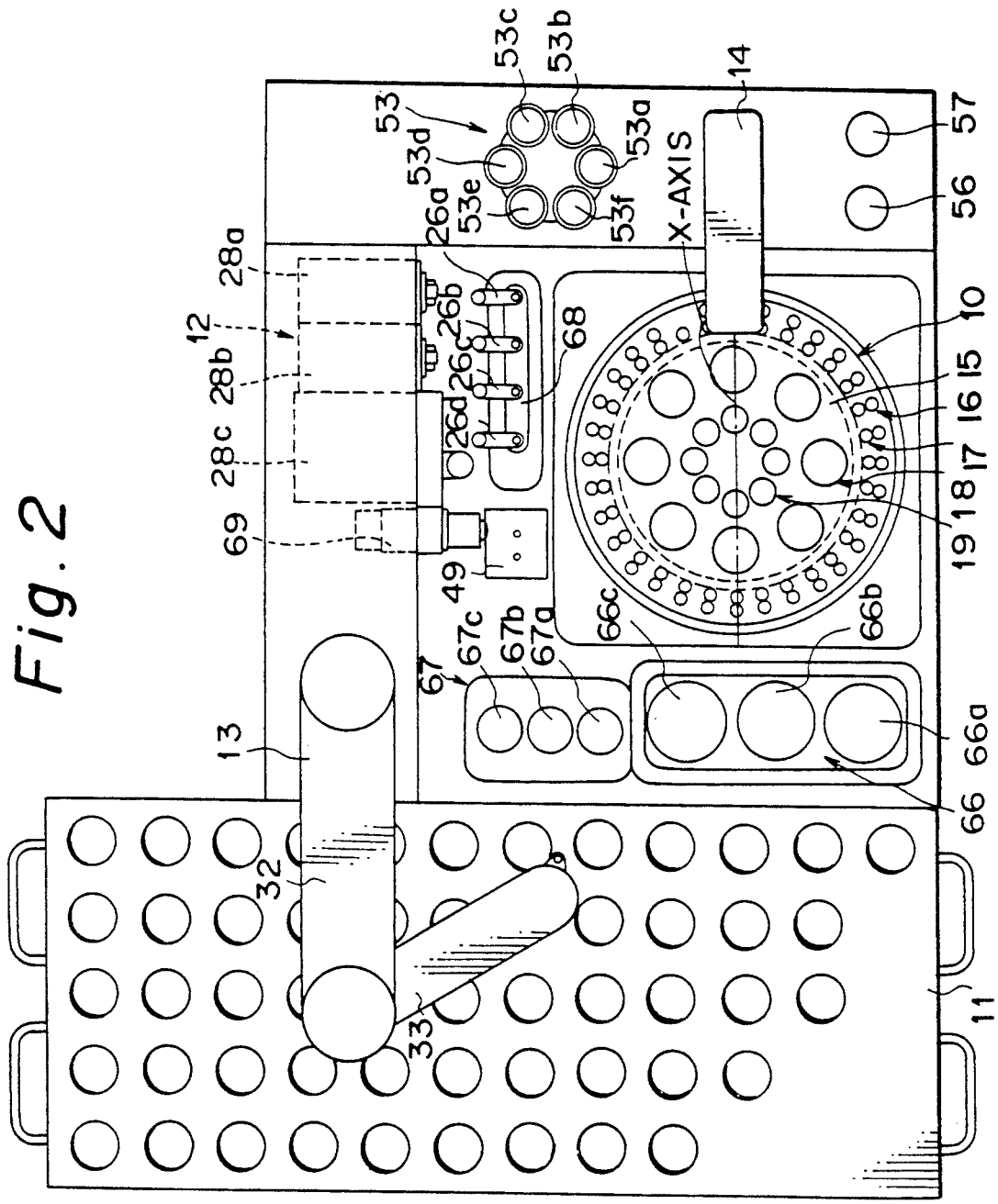
FIG. 2 is a plan view of the arrangement of the automatic preparation apparatus in the embodiment of FIG. 1.
Figure 3:
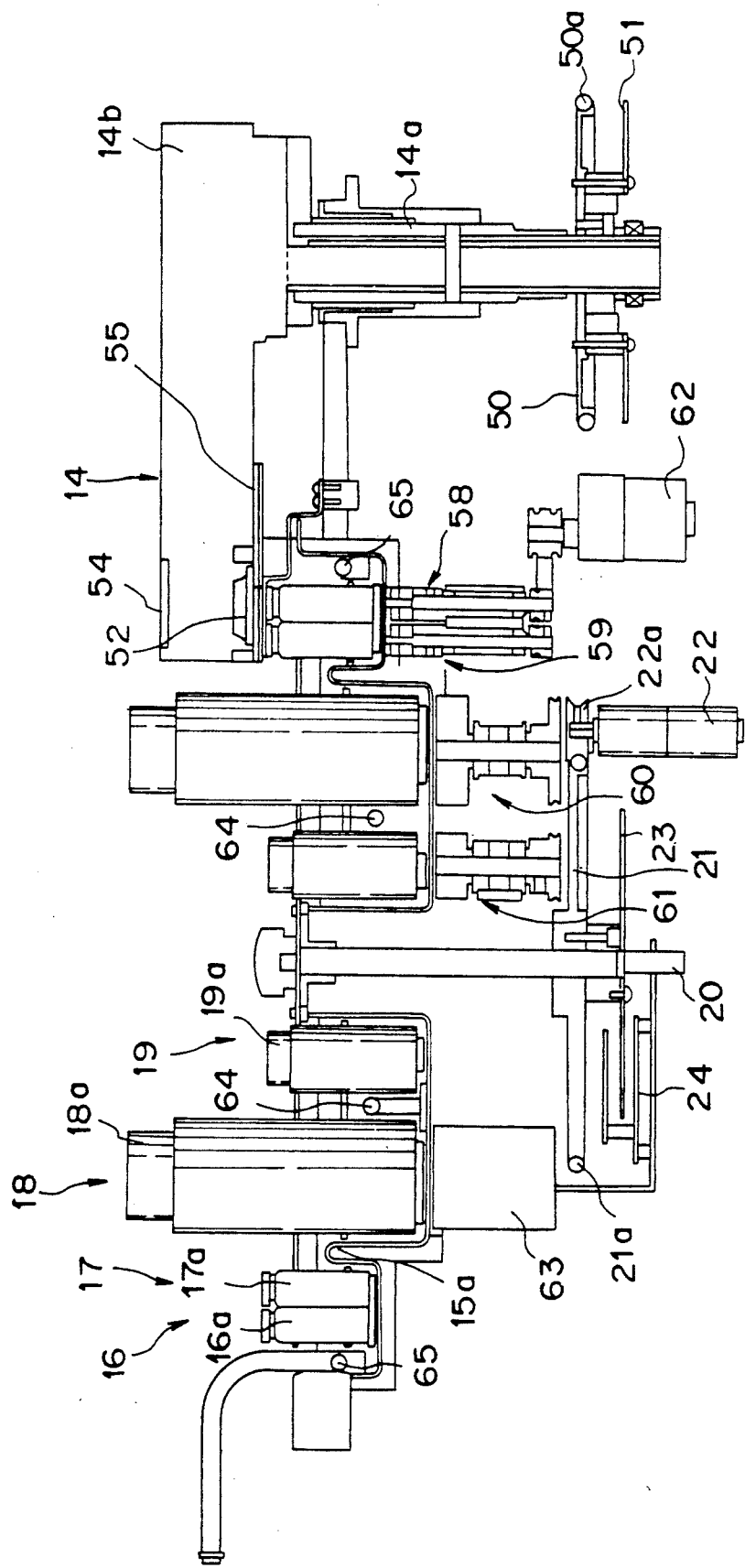
FIG. 3 is a partial cross sectional view of the embodiment of FIG. 1.

FIG. 1 is a perspective view schematically showing the arrangement of a preferred embodiment of FIG. 1. FIG. 2 is a plan view of the embodiment. FIG. 3 is a partial cross sectional view of the embodiment of FIG. 1.

The apparatus according to this embodiment chiefly comprises turntable means 10, rack means 11, probe means 12, robot means 13, filter robot means 14, and control means (not shown in FIG. 1) for controlling those means.

The turntable means 10 includes a turntable 15 that has container storage regions arranged in multiple circular rows (four rows in the present embodiment). As FIG. 2 clearly shows, a plurality (32 pieces in the present embodiment) of filtrate containers (16a for example) are mounted in the storage region 16 in the outermost row (filtration row), and a plurality (32 pieces in the present embodiment) of containers (17a for example) for containing the liquid under treatment are mounted in the container storage region 17 in the row second from the outermost row. In addition, a plurality (8 in the present embodiment) of sample containers (18a for example) for containing the sample liquid are mounted in the container storage region 18 in the third row (sample row) from the outermost row, and a plurality (8 in this embodiment) of containers (19a for example) for dilution are mounted in the container storage region 19 in the innermost row (dilution row). It ought to be noted that in FIG. 1, only some of the container storage regions and the containers are illustrated, and most of them are omitted for ease of understanding of the arrangement.

The containers 16a and 17a mounted in the container storage region 16 in the filtration row and in the container storage region 17 in the transfer row each have a capacity of a maximum of about 20 ml, but the sample containers 18a mounted in the container storage region 18 in the sample row may each have a capacity of a maximum of about 150 ml. The containers 19a mounted in the container storage region 19 in the dilution row may each have a capacity of a maximum of 50 ml. The numbers of mountable containers in the container storage regions in the respective rows are not restricted to the above-mentioned numbers, but may be any number.

As shown in FIG. 3, the turntable, which is fixed to a rotating shaft 20, is so arranged that it is turned together with the rotating shaft 20 in a horizontal plane and can stop accurately at a desired position. The rotating shaft 20 is rotated by turning a drive disc 21, provided therebelow, with an electric motor 22. In this embodiment, the rotation of the rotating shaft 20 is effected through the intermediary of a rubber ring 21a, provided along the outer periphery of the drive disc 21, which rubber ring is turned around by a roller 22a of the electric motor 22. A gear drive or belt drive may be used other than this combination of the rubber ring and roller. When an ordinary AC or DC motor is used for the electric motor 22, the marks previously provided on a surface of a position mark disc 23 are detected by an optical sensor 24 for feedback control of the position of the turntable 15. If a stepping motor is used for the electric motor, this sensor can be omitted.

The rack means 11 is provided in a stationary state in a position different from the turntable 15 and is so arranged as to accommodate many sample containers. The rack means 11 can be dismounted from the apparatus for transportation. Therefore, on completion of a series of treatment steps, a large number of sample containers can be exchanged at the same time. In FIG. 1, only some of the container storage regions and containers are shown for easier understanding of the arrangement, and most of them are omitted.

Figure 4:
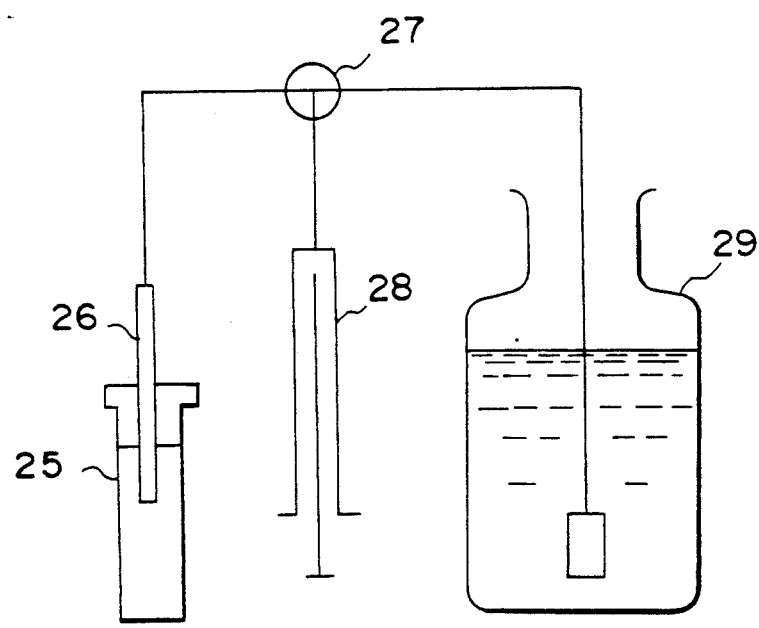
FIG. 4 shows the probe means in the embodiment in FIG. 1.

As shown in FIG. 4, the probe means 12 comprises a probe needle 26 for sampling and injecting the sample liquid, diluting water or the like contained in the container 25 by a predetermined amount, and a microsyringe pump (diluter) 28 connected through a three-way change-over valve 27 to a probe needle 26. The microsyringe pump 28 is of known type and sucks and discharges a predetermined amount of liquid. The three-way change-over valve 27 is also connected to a diluting water tank 29. As shown in FIGS. 1 and 2, in this embodiment, there are provided four kinds of probe needles 26a, 26b, 26c and 26d, which differ in the diameter of the needle portion, and one of those probe needles is selected and used. Which of the probe needles is used is determined according to the properties of the sample liquid. For injecting into the liquid chromatography system that will be described later, a thin-diameter probe needle is selected. Each of the probe needles is connected to small syringe pumps 28a and 28b and a large syringe pump 28c through an extendible flexible pipe and a change-over valve, which are not shown. The selection and the horizontal and vertical movements of the probe needles 26a, 26b, 26c and 26d are controlled by the robot means 13 to be described later.

As shown in FIG. 1, the robot means 13 holds a sample container 30 with the fingers 31 that are an attachment and transfers the container between the container storage region 18 on the turntable 15 and the container storage region on the rack means 11. The robot means 13 moves a probe needle to a desired position in the horizontal or vertical direction. In addition, the robot means 13 is used to select one of multiple kinds of filters as described later. In this embodiment, for the robot means 13, a horizontal two-joint robot is used which is capable of accurate position control to a desired two-dimensional (X-axis, Y-axis) position in an arm-reaching range, and which is also capable of position control in the vertical (Z-axis) direction. Generally, the horizontal two-joint robot has a great compliance in the horizontal direction and high rigidity in the vertical direction.

Figure 5:
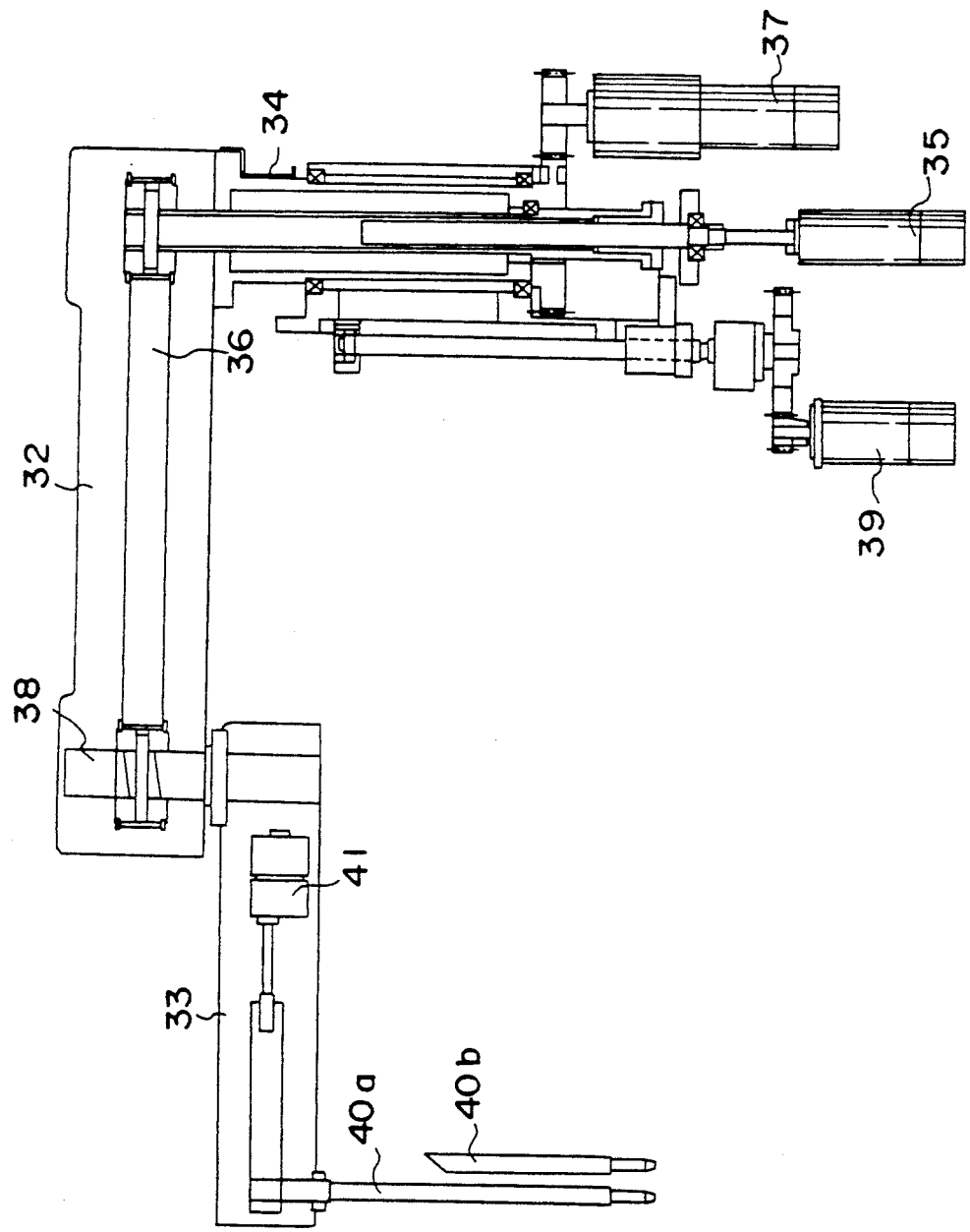
FIG. 5 is a cross sectional view of a horizontal two-joint robot in the embodiment of FIG. 1.

FIG. 5 is a cross sectional view of this horizontal two-joint robot. Reference numeral 32 denotes a first arm, and 33 denotes a second arm. The first arm 32 can rotate in the horizontal direction as it is driven by a motor 35. The second arm 33 is pivotally supported on bearings at the distal end of the first arm, and can rotate about a support shaft 38 in the horizontal direction as it is driven by a motor 37 through a drive system 36 such as a belt. The whole horizontal two-joint robot is driven vertically by a motor 39. Two chuck members 40a and 40b for chucking the fingers for holding a sample container or a probe needle are detachably mounted at the distal end of the second arm 33. The distance between the chuck members 40a and 40b is controlled by the drive of a motor 41 provided in the second arm 33. Though they are not shown, the robot means 13 are provided with an encoder for detecting the rotational position of the motor 35 for the first arm 32, an encoder for detecting the rotational position of the motor 37 for the second arm 33, sensors for detecting an overrun and the home positions of the first arm 32 and the second arm 33 in the horizontal direction, and sensors for detecting an overrun and the home positions of the two arms in the vertical direction.

Figure 6:
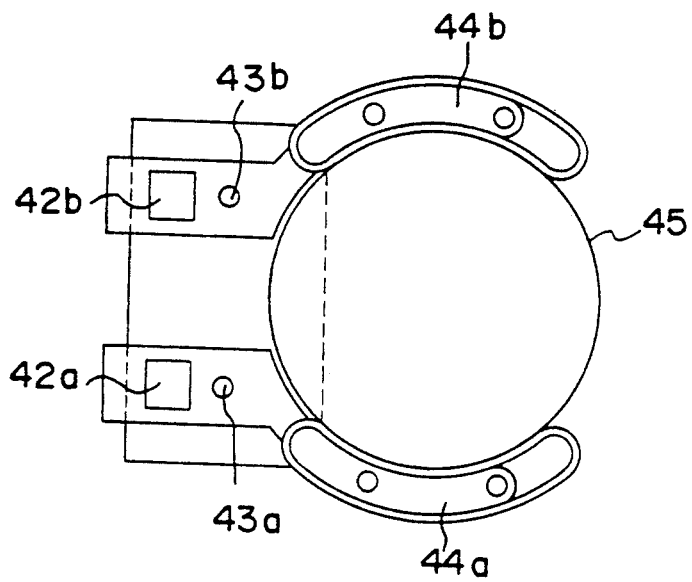
FIG. 6 shows an example of the fingers as attachment for holding a sample container.
Figure 7:
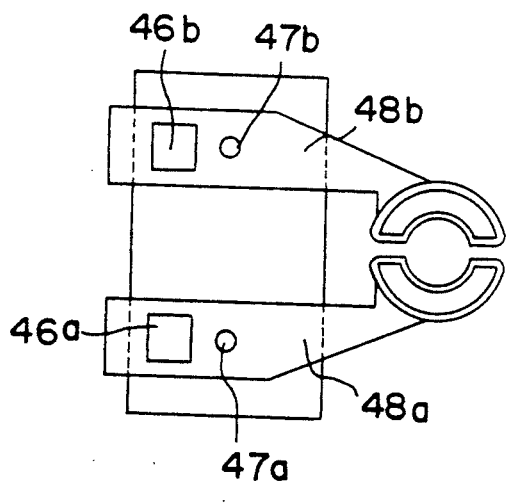
FIG. 7 shows an example of the fingers as attachment for holding a probe needle.

FIG. 6 shows an example of the fingers as an attachment for holding a sample container. The fingers are so arranged that the distal end portions of the chuck members 40a and 40b are inserted into holes 42a and 42b. When the chuck members 40a and 40b are moved in the direction in which the distance between the chuck members is elongated or narrowed, the finger members 44a and 44b are turned about fulcrums 43a and 43b to hold or release a sample container 45. FIG. 7 shows an example of the fingers as an attachment for holding a probe needle. Like in FIG. 6, the fingers are so arranged that the distal end portions of the chuck members 40a and 40b are inserted into holes 46a and 46b. When the chuck members 40a and 40b are moved in the direction in which the distance between the chuck members is elongated or shortened, the finger members 48a and 48b are turned about fulcrums 47a and 47b to hold or release a probe needle. Pairs of fingers are placed at a specified position 49 (FIG. 2) within the movable range of the chuck members 40a and 40b, and a pair of the fingers is automatically connected with the chuck members 40a and 40b as occasion demands.

As shown in FIG. 3, the filter robot means 14 chiefly comprises a vertically extending support post member 14a and an arm member 14b that extends horizontally from the top of the support post member 14a. The support post member 14a serves also as a rotating shaft, and as the support post member 14a rotates, the arm member 14a turns around. The support post member 14a is rotated by turning a drive disc 50, provided therebelow, with an electric motor, not shown. In this embodiment, the rotation of the support post member 14a is effected through the intermediary of a rubber ring 50a provided along the outer periphery of the drive disc 50, which rubber ring is turned around by a roller of an electric motor. A gear drive or belt and pulley drive may also be used other than a combination of a rubber ring and a roller. When an ordinary AC or DC motor is used for the electric motor, the marks previously provided on a surface of a drive disc 51 fixed to the support post member 14a are detected by an optical sensor for feedback control of the rotational position of the filter robot means 14. If a stepping motor is used for the electric motor, this sensor can be omitted.

The arm member 14b is so arranged that it can not only be turned about the support post member 14a in the horizontal plane, but also the distal end portion of the arm 14 can move vertically while the arm member 14b is turned about that part thereof mounted to the support post member 14a for a predetermined angle in a vertical plane. By this arrangement, during a filtering process, the distal end (outlet end) of a filter to be described later can be inserted into the inside of the container, so that even a part of the filtered liquid is prevented from flowing out of the container. This rotating motion can be achieved by a rotation moment applied to the arm member 14b by an air cylinder, not shown, which reciprocates by the compressed air.

The arm member 14b is provided at its distal end with filter holding mechanism for releasably holding a disposable formed filter 52, a sealing mechanism for defining a sealing chamber at the side of the disposable filter where the sample liquid is injected and a mechanism for feeding the compressed gas into this sealing chamber.

The filter holding mechanism is so arranged that it holds a disposable filter 52 from below by abutting against part of the lower surface of the filter 52 supplied from the filter supply unit 53 (FIG. 1) through an insertion aperture 54 at the upper surface of the distal end of the arm member 14b. A holding member 55, which is coupled via a rod to a pneumatic cylinder reciprocating in the front-rear direction, supports part of the lower surface of the disposable filter. When the disposable filter 52 is discarded, the holding member 55 is moved to allow the disposable filter 52 to drop by its own weight. The arrangement of the filter holding mechanism, sealing mechanism and the mechanism for feeding the compressed gas mentioned above is described in detail in U.S. Pat. No. 4,951,513.

The filter robot means 14 is provided with a sensor for detecting the rotational position of the arm member 14b in the horizontal direction, a sensor for detecting the rotational position of the arm member 14b in the vertical direction, and a sensor for determining whether the filter robot means 14 holds a disposable filter 52 or not, though those sensors are not shown.

The arm member 14b of the filter robot means 14 can turn in the horizontal direction as the support post member 14a, and four stop positions of the arm member 14b are provided in this embodiment. One of the four stop positions is located at the treating position (on the X-axis) shown in FIGS. 1 and 2, and the arm member 14b is stationary at this position while the sample is being filtered. In this case, the outlet end of the disposable filter 52 is located so as to be right above the container storage region 16 in the filtration row. The arm member 14b is capable of stopping at the position of a filter storage magazine 53a of the filter supply unit 53 shown in FIG. 2. In this embodiment, the filter supply unit 53 is provided with six filter storage magazines 53a to 53f. Each of the filter storage magazines 53a to 53f is arranged to accommodate multiple unused disposable filters of different kinds (16 pieces in this embodiment).

When mounting disposable filters in the filter robot means 14, the insertion aperture 54 of the arm member 14b is moved first to a position right below the filter storage magazine 53a. A disposable filter is caused to come down from the filter storage magazine 53a through the insertion aperture 54, and the filter is held by the filter holding mechanism. When mounting a disposable filter of a different kind, the filter supply unit 53 is rotated to move a desired filter storage magazine to a currently indicated position of the filter storage magazine 53a. This movement of the filter supply unit 53 is achieved by the arm of the filter robot means 13 pushing the filter supply unit 53 to rotate.

Other stop positions of the arm member 14b are located at a discharge port 56 for discharging the filtered diluting water and a discard port 57 for discarding used filters (FIGS. 1 and 2).

As shown in FIG. 3, agitators 58, 59, 60 and 61 are disposed right below the container storage region 16 in the filtration row, the container storage region 17 in the transfer row, the container storage region 18 in the sample row and the container storage region 19 in the dilution row, under the turntable 15 and between the turntable rotating shaft 20 and the filter robot support post 14a serving as its rotating shaft (on the X-axis). Those agitators 58, 59, 60 and 61 are known magnet-driven types for agitating the sample in the containers when the containers are located in the respective storage regions. That is, S-pole and N-pole are provided at the radial ends of the upper portions of the agitators and are rotated by an electric motor 62 to agitate the magnetic particles (stirrers) contained in the containers. To dissolve and disperse the sample, an ultrasonic oscillator 63 is provided right below the sample container storage region 18 on an extension of a line connecting the turntable rotating shaft 20 and the filter robot support post 14a (on the X-axis) and below the turntable 15.

As shown in FIG. 3, the turntable 15 has a partition 15a which separates the container storage region 16 in the filtration row and the container storage region 17 in the transfer row from the container storage region 18 in the sample row and the container storage region 19 in the dilution row. A resistance coil 64 for heating is disposed between the sample row and the dilution row, while a cooling liquid circulation pipe 65 for cooling is disposed along the outer periphery of the outermost filtration row. The sample liquid and the diluted solution are stored in the container storage region 18 in the sample row and in the container storage region 19 in the dilution row, respectively, and therefore, by heating these kinds of liquid, the extraction efficiency can be improved (the heating block). The filtered solution and the solution under treatment are stored in the container storage region 16 in the filtration row and in the container storage region 17 in the transfer row, respectively, and therefore, to cool these regions to prevent these solutions from being heated and condensed, the partition 15a and the cooling liquid circulation pipe 65 are provided (the cooling block). Since the heating and cooling blocks are separated by a partition, the heating and cooling effects are very high.

The apparatus according to this embodiment is further provided with reagent stations 66 and 67 (FIGS. 1 and 2) in a stationary position outside the turntable 15, where reagent containers 66a to 66c of extra-large capacity (500 to 1000 ml) and reagent containers 67a to 67c of large capacity (150 ml) can be stored.

A cleaning mechanism 68 is provided at the storage position of the probe needles 26a, 26b, 26c and 26d. The cleaning mechanism is intended for cleaning the probe needles 26a, 26b, 26c and 26d elements communicating therewith, and at least during the cooling operation, a cleaning liquid flows from the cleaning liquid supply and discharge system, not shown.

In addition, an automatic six-way change-over valve 69 is provided, which serves as the input port for injecting the sample into liquid chromatography system. In the figures, only one input port is shown, but a plurality of input ports may be provided when necessary.

Figure 8B:
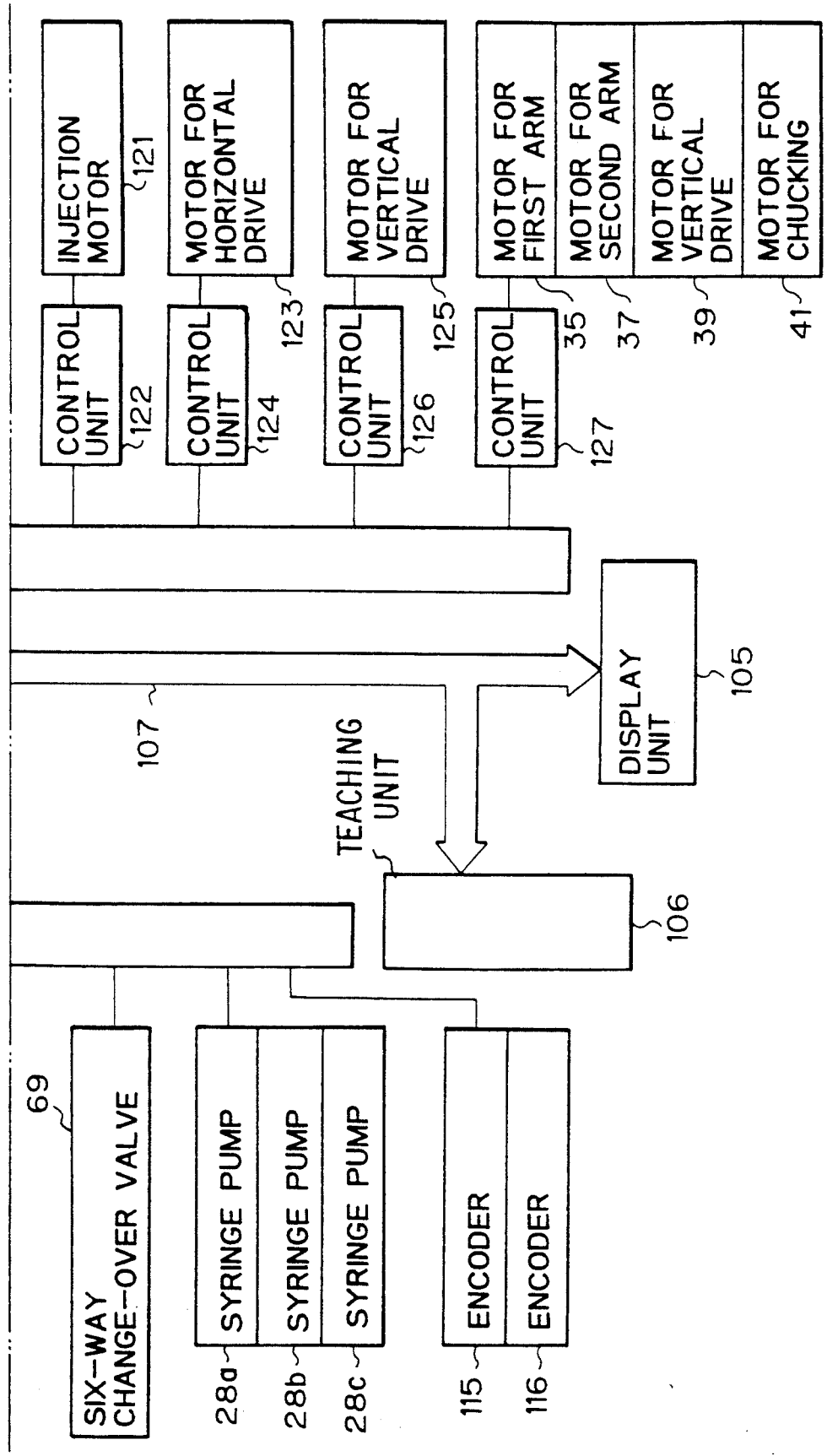
FIG. 8 composed of FIGS. 8A and 8B is a schematic representation of the electrical arrangement of the control means in the embodiment in FIG. 1.

FIG. 8 composed of FIGS. 8A and 8B is a block diagram schematically showing the electrical constitution of the control means used in this embodiment. As is evident from the figure, in this embodiment, a microcomputer is used which comprises a central processing unit (CPU) 100, read only memory (ROM) 101, random access memory (RAM) 102, input/output (I/O) interfaces 103 and 104, display unit 105, teaching unit 106, and bus 107 for connecting those parts.

The I/O interface 103 is connected with a sensor 108 for detecting the horizontal rotational position of the arm member 14b of the filter robot means 14, a sensor 109 for detecting the vertical rotational position of the arm member 14b, a sensor 110 for determining whether the filter robot means 14 holds a filter, a sensor 111 for detecting a horizontal overrun of the arm of the robot means 13, a sensor 112 for detecting the horizontal home position of the robot means arm, a sensor 113 for detecting a vertical overrun of the robot means arm, and a sensor 114 for detecting the vertical home position of the robot means arm. Detected information signals are input into the microcomputer. The I/O interface 103 is further connected with an ultrasonic oscillator 63, a three-way change-over valve 69 of the liquid chromatography system, and syringe pumps 28a, 28b and 28c. Those parts are controlled by signals from the microcomputer. The I/O interface 103 is also connected with encoders 115 and 116 of the robot means 13 to control the position of the robot means 13. The I/O interface 104 is connected with a control unit 117 for controlling the rotation of a stepping motor 22 for the turntable 15, and the position of the turntable 15 is controlled by the microcomputer. The I/O interface 104 is further connected with a control unit 118 for controlling the motor 62 for the agitators 58, 59, 60 and 61, a control unit 120 for controlling a motor 119 of a cleaning liquid drive pump for the cleaning mechanism 68, a control unit 122 for controlling an injection motor 121 for the six-way change-over valve 69, a control unit 124 for controlling a motor 123 for horizontally driving the arm member 14b of the filter robot means 14, a control unit 126 for controlling a motor 125 for vertically driving the filter robot arm member 14b, a motor 35 for driving the first arm 32 of the robot means 13, a motor 37 for driving the second arm 33 of the robot means 13, a motor 39 for vertically driving the arms 32 and 33, and a control unit 127 for controlling the motor 41 for chucking the fingers. Those parts are controlled by signals from the microcomputer.

Figure 9:
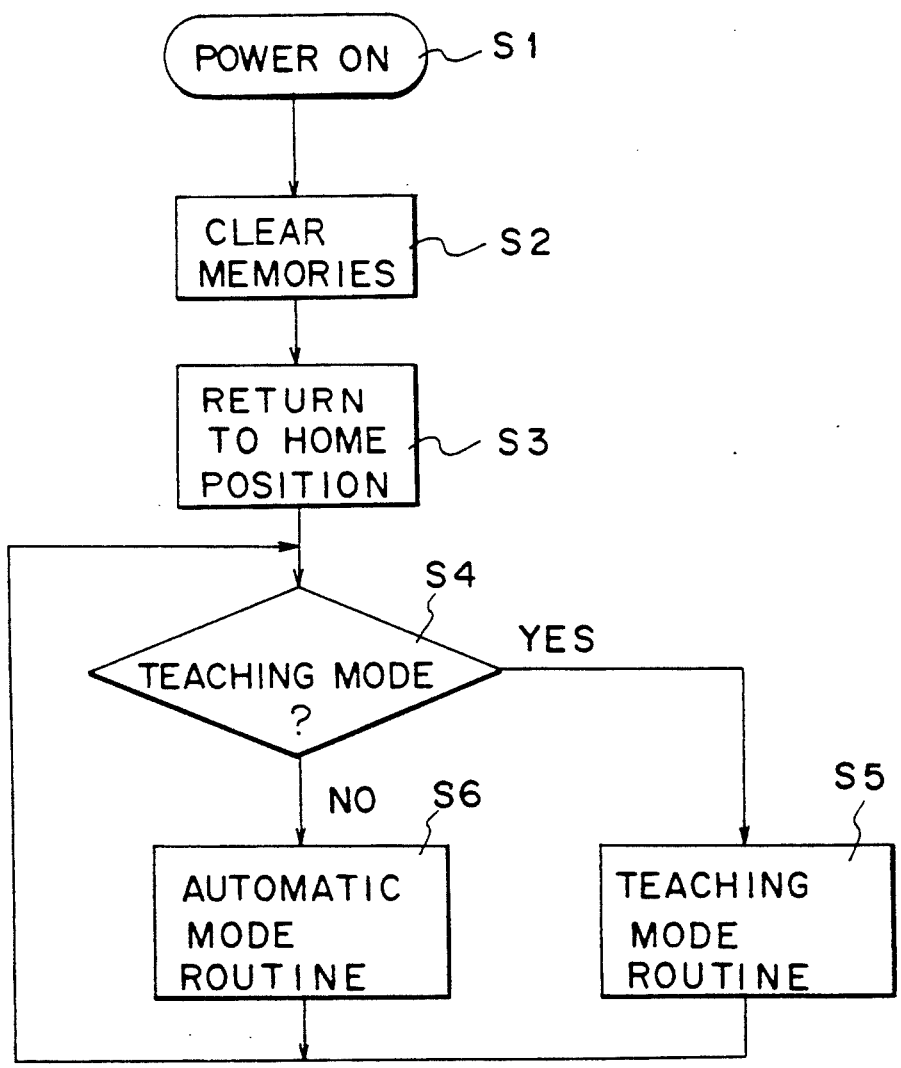
FIG. 9 is a flowchart schematically showing an example of a control program of a microcomputer in the embodiment of FIG. 1.

The operation of this embodiment will next be described. FIG. 9 is a flowchart schematically showing an example of a control program of the microcomputer.

When the power supply is turned on (step S1), the CPU clears the RAM 102 and other memories (step S2), and then resets all the drive elements to their home positions (original positions) (step S3). More specifically, with respect to the turntable means 10, a group of containers to be started is restored to the treating position (on the X-axis); with respect to the robot means 13, the arms are positioned at the specified home positions; and with respect to the filter robot means 14, the arm 14b is turned to the position of filter supply unit 53. Then, a decision is made whether a teaching process is to be performed (step S4), and if the teaching process is performed, the program proceeds to the teaching mode routine (step S5). If the teaching process is not performed, the program moves on to the automatic mode routine (step S6).

The teaching process, which sets an address for a position to which the robot means 13 is moved, is carried out by the teaching unit 106.

Figure 10:
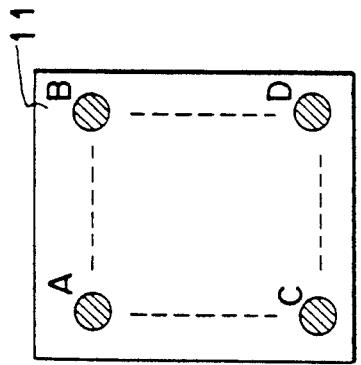
FIGS. 10 to 12 are views for explaining the teaching process in the embodiment of FIG. 1.
Figure 11:
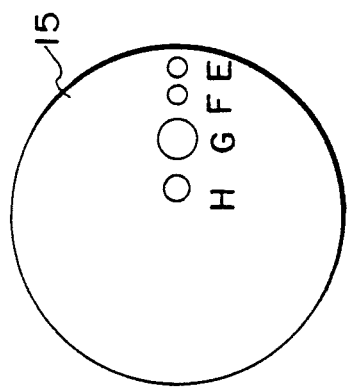

With regard to the teaching process of the storage positions in the horizontal direction, description will first be made of address setting for the position of the sample container storage region in the rack means 11. As shown in FIG. 10, sample container storage positions are arranged in matrix form on the rack means 11. The center of the fingers attached to the distal end of the second arm 33 of the robot means 13 is moved manually to points A, B, C and D at the four corners of this matrix arrangement to store their addresses in memory. This process makes it possible to calculate the addresses of the center positions of the remaining sample container storage positions. With regard to the teaching process of the horizontal container storage positions on the turntable 15, as shown in FIG. 11, the distal end of the robot means 13 is moved manually to points E, F, G and H, which are the container storage positions in each row of the treating position (on the X-axis) to store their addresses in memory. This process makes it possible to calculate the addresses of the center positions of the container storage positions on the turntable 15.

Figure 12:
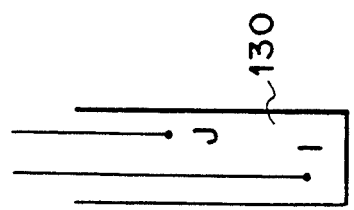

With regard to the teaching process of the positions in the vertical direction, as shown in FIG. 12, a probe needle attached to the distal end of the second arm 33 of the robot means 13 is lowered by a motor which is operated by manual operation into a container 130 placed in the container storage regions on the turntable 15 and the reagent stations 66 and 67 in order to store the addresses in the vertical direction (in the Z-axis direction) at the sucking and discharging positions. This process is done for the containers of different kinds.

The automatic mode routine includes (a) the filtration/dilution mode in which the sample solution is filtered and then diluted, (b) the dilution/filtration mode in which the sample solution is diluted and then filtered, (c) the filtration mode in which the sample solution is only filtered, (d) the multiple-stage filtration mode in which the sample solution is filtered in multiple stages, (e) the primary dilution mode and the secondary dilution mode in which the sample solution is only diluted, (f) the reaction mode in which the reaction of the sample solution with a reagent is examined, (g) the dissolution/filtration mode in which the sample is dissolved and filtered, (h) the injection mode in which the sample solution is automatically injected into the input port of the liquid chromatography system, and (i) the mode in which a creamy sample is extracted and filtered, and automatically injected into the input port of the liquid chromatography system. Description will be made of the dissolution-dilution-filtration-injection mode which is formed by combining parts of the above-mentioned modes.

Figure 13B:
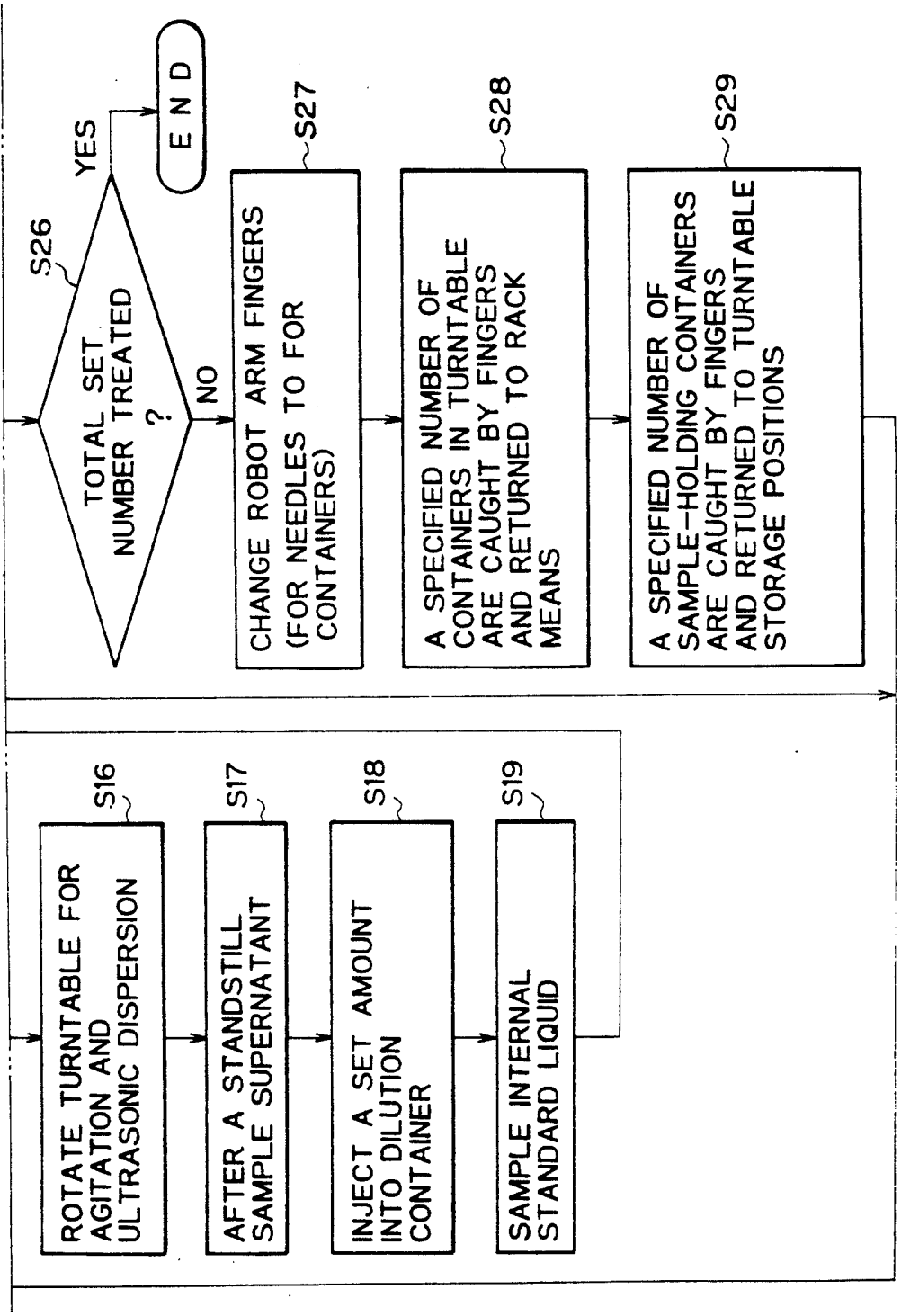
FIG. 13 composed of FIGS. 13A and 13B is a flowchart showing the flow in the mode of dissolution-extraction-dilution-filtration-injection in the embodiment of FIG. 1.
Figure 14:
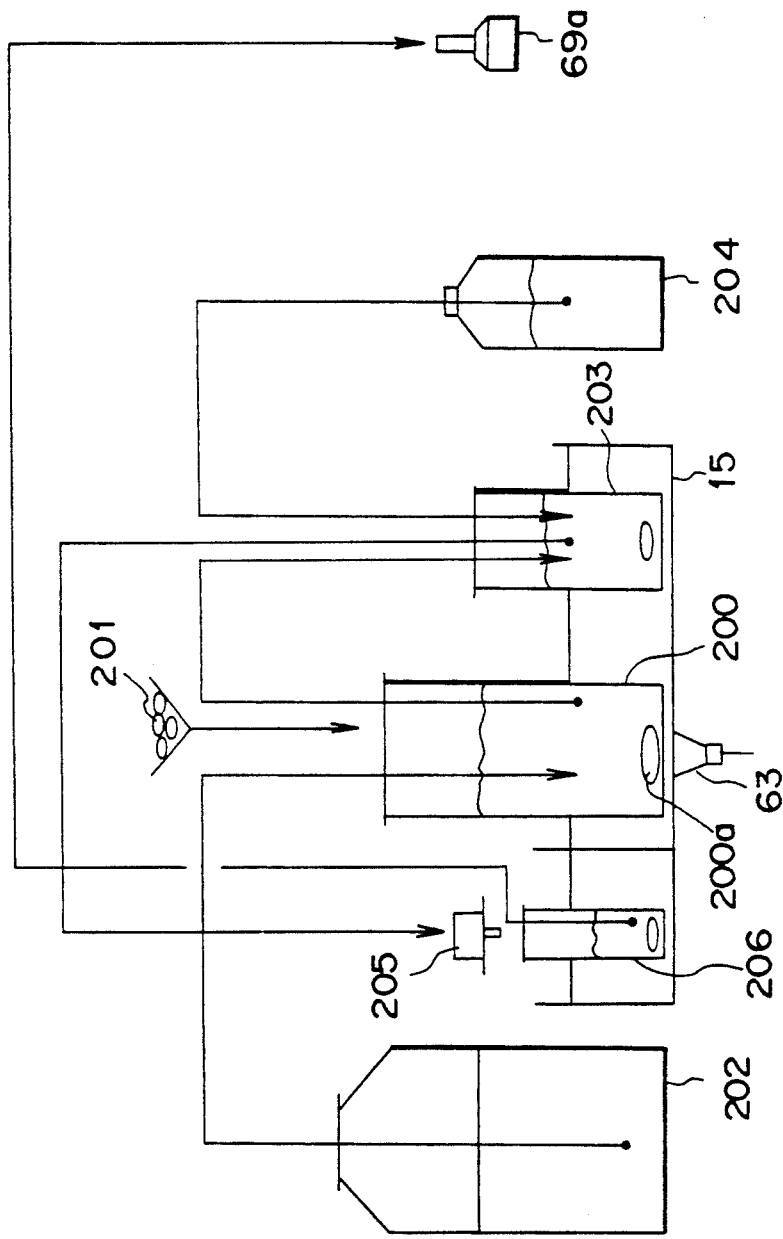
FIG. 14 shows an operation sequence of the mode of FIG. 13.

FIG. 13 composed of FIGS. 13A and 13B is a flowchart showing the flow of this dissolution-extraction-dilution-filtration-injection mode. FIG. 14 shows the operation sequence of this mode.

This mode is used in tablet purity test and content uniformity test. At step S10, a tablet as a sample is put into a sample container 200 in the sample row on the turntable 15. At the next step S11, an initial process for the syringe pump is performed, and at step S12, the home position of the arm of the robot means 13 is checked. At the subsequent step S13, the arm of the robot means 13 is moved to a specified position where fingers are located and after the fingers for holding a probe needle are chucked, a probe needle of a desired diameter is selected and held.

At step S14, the dissolved liquid is sampled from a dissolved liquid container 202 of an extra-large capacity and put into the syringe pump. This dissolved liquid container 202 is connected by pipe to the syringe pump through the three-way change-over valve, and the sampled dissolved liquid is injected into a container 200 by a predetermined amount at step S15. This partial injection is performed with a probe needle that is moved by the robot means 14 to the position of the sample container 200. At step S16, the turntable 15 is turned around to position the sample container 200 to right above the agitator 60 to dissolve the sample, and then the turntable 15 is turned to position the sample container 200 to right above the ultrasonic oscillator 63 for dispersion by ultrasonic drive. In FIG. 14, numeral 200a denotes a stirrer. After the sample container is kept still for a sufficiently long time, at step S17 the supernatant is sampled through a probe needle. At step S18, the probe needle is moved to the position of a dilution container 203 in the dilution row on the turntable 15, and a set amount of the sample supernatant is put into this dilution container 203. At step S19, the probe needle is moved to the position of an internal standard solution container 204 stored in the reagent station 67 by the side of the turntable, and the internal standard solution is sampled. At step S20, the probe needle is moved to the position of the dilution container 203, and the sampled internal standard solution is injected into the dilution container 203 by a set amount. At the next step S21, after agitated, the diluted solution in the dilution container 203 is sampled by a set amount.

At step S22, the probe needle is moved to the position of a filter 205 in the filter robot means 14, and the sampled diluted solution is injected into the filter 205. A desired filter 205 supplied from the filter supply unit 53 is to be previously set in the filter robot means 14. In addition, the filter robot means 14 is to have been turned so that a filter container 206 in the filtration row on the turntable 15 is located below the filter 205. At step S23, the diluted solution is injected into the filtrate container 206 while it is filtered under pressure.

At step S24, the filter robot means 14 is moved from the treating position to bring the probe needle to the position of the filtrate container 206, and the filtered liquid is sampled. The probe needle is moved to the position of the input port 69a of the change-over valve 69 of the liquid chromatography system, and the sampled filtered liquid is injected into the input port 69a.

At step S25, a decision is made whether the treatment of this mode has been finished for the set number (a maximum of 8 in this embodiment) of sample containers stored on the turntable 15. If the number of treated samples is smaller than the set number, the program goes back to step S14, and the steps S14 to S24 mentioned above are repeated. If the number of treated samples has reached the set number, the program proceeds to step S26, where a decision is made whether the number of treated samples has reached the total set number. If the total set number has been reached, the treatment in this mode is finished.

If the number of treated samples has not reached the total set number, the sample containers on the turntable 15 are changed with new sample containers in the rack means 11. To begin with, at step S27, the arm of the robot means 13 is moved to a specified position where fingers are placed, and the fingers for holding a probe needle are changed for fingers for holding a container. At step S28, a sample container stored on the turntable 15 is caught by the fingers for holding a container, and transferred to a specified storage position in the rack means 11. A specified number of sample fingers are transferred in the same manner. At step S29, a new sample container, which contains the sample, set in the rack means 11 is caught by the fingers for holding a container, and is transferred to a storage position in the sample row on the turntable 15. Also, in this case, a specified number of sample containers are transferred in the manner as described above. Now, the program returns to step S14, and steps S14 to S24 are repeated.

In the treatment mode shown in FIG. 13, probe needles are cleaned by the cleaning mechanism 68 as necessity requires. The cleaning method is well-known, and description of it is omitted.

Description will now be made of the two-stage filtration mode in which the sample liquid is filtered in two stages.

Figure 15:
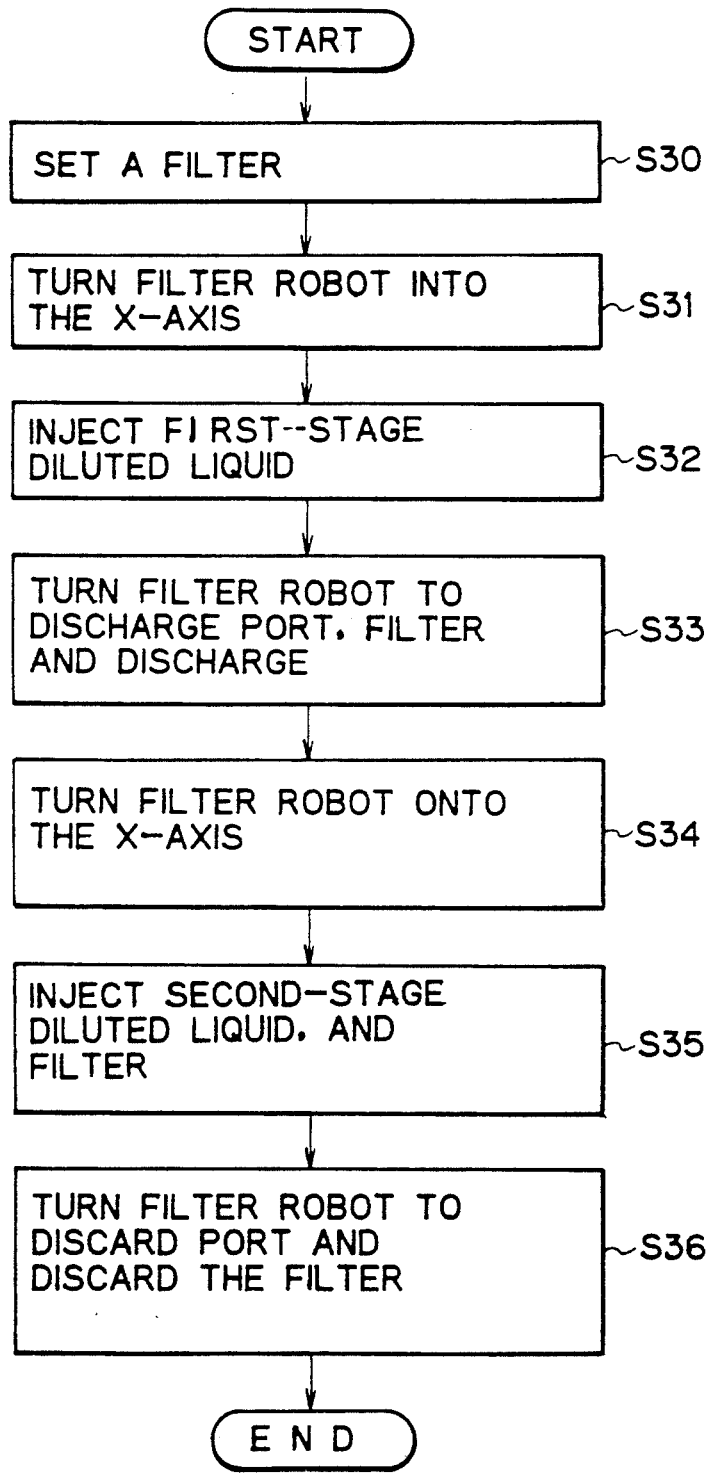
FIG. 15 shows a flow of the two-stage filtration mode in the embodiment of FIG. 1.

FIG. 15 is a flowchart showing the flow of the motions in the two-stage filtration mode. FIGS. 16a to 16e are views for explaining the operation of the probe means 12, the robot means 13 and the filter robot means 14 in this mode. FIGS. 17a to 17f show the behavior of the liquid inside the probe needle in this mode.

This mode provides a two-stage filtration in which the filtered liquid of the first filtering session is discarded and the filtered liquid of the second session is obtained in order to prevent part of the components of the sample from being absorbed by the membrane of the filter during the filtration process. At step S30, the filter robot means 14 is turned to the position of the filter supply unit 53, and a desired kind of filter 52 is set in the filter robot means 14 (the state in FIG. 16a). At step S31, the filter robot means 14 is turned onto the X-axis. At step S32, a probe needle 26 is moved by the robot means 13 to the position of the filter 52 in the filter robot means 14, and a predetermined amount of the sampled diluted liquid of the first stage is injected into the filter 52 (the state in FIG. 16b). At step S33, the filter robot means 14 is turned to position the filter 52 right above the discharge port 56, and under this condition, the liquid is filtered under pressure, and the filtered liquid is discharged into the discharge port 56 (the state in FIG. 16c).

At step S34, the filter robot means 14 is turned to come to be on the X-axis, so that a filtrate container in the filtration row of the turntable 15 is right below the filter 52. At step S35, a probe needle 26 is moved by the robot means 13 to the position of the filter 52 in the filter robot means 14, a set amount of the sampled diluted liquid of the second stage is injected into the filter 52, filtered under pressure and injected into the filtrate container (the state in FIG. 16d). At step S36, the filter robot means 14 is turned to position the filter 52 right above the discard port 57, and under this condition, the filter 52 is dropped and discarded (the state in FIG. 16e).

In this mode, the liquid is sucked in and discharged as shown in FIGS. 17a to 17f. In the initial state, air and diluting water are contained as shown in FIG. 17a. Then, 200 $\mu$l of dilution preventive liquid sucked in (FIG. 17b). After this, 200 $\mu$l of the diluted liquid of the first stage is sucked (FIG. 17c). This diluted liquid is injected into the filter 52 (FIG. 17d). Then, 1500 $\mu$l of the diluted liquid of the second stage is sucked in (FIG. 17e). This diluted liquid is injected into the filter 52 (FIG. 17f).

The filtration of multiple stages in the present invention is not limited to the two stages mentioned above, but may be three stages or any greater number of stages. In such a case, filtration of the first stage mentioned above is repeated.

Description will next be made of the mode of extracting, filtering and then automatically injecting a creamy sample into the input port of the liquid chromatography system.

Figure 18:
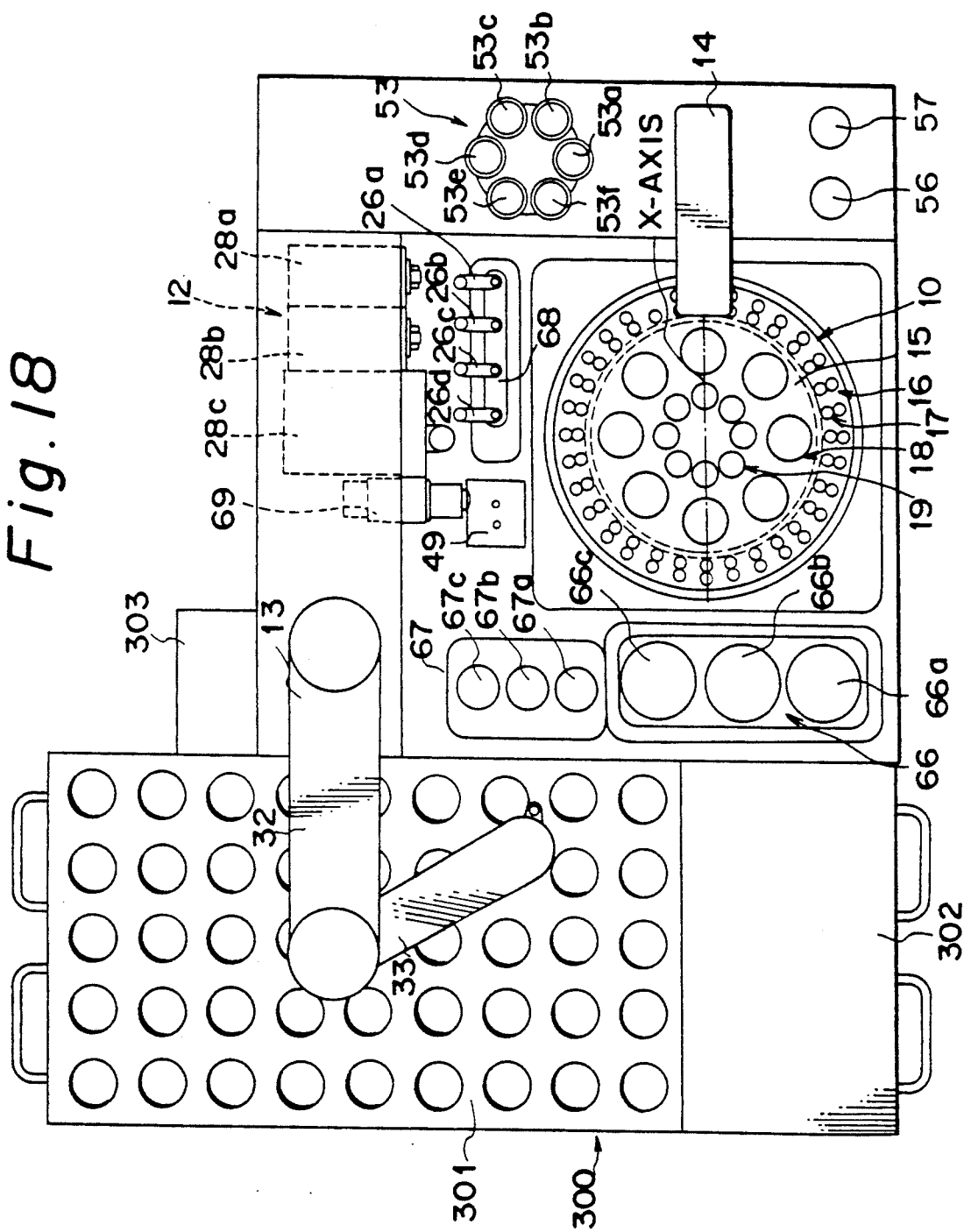
FIG. 18 is a plan view of the arrangement of the automatic preparation apparatus in the mode of pretreating a creamy sample.
Figure 19:
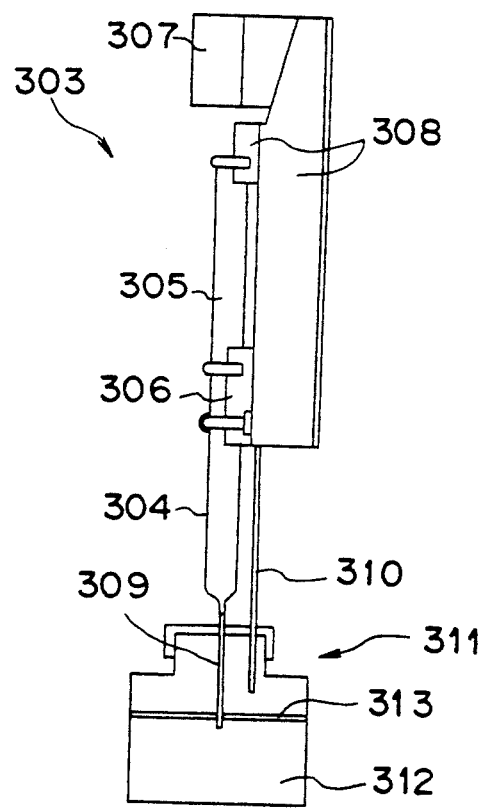
FIG. 19 is a diagram for explaining the arrangement and operation of the plunger pump.

FIG. 18 is a plan view of the arrangement of the automatic preparation apparatus in this mode. FIG. 19 is a diagram for explaining the arrangement and operation of the plunger pump. The automatic preparation apparatus of FIG. 18 is almost identical with that of FIG. 2, excepting the differences as follows. In the automatic preparation apparatus of FIG. 18, as rack means 300, a rack table 301 and an automatic scale 302 are installed, and a plunger pump 303 is added for sampling a creamy substance.

As shown in FIG. 19, in the plunger pump 303, a disposable housing comprising a cylinder member 304 and a piston member 305 is mounted detachably to the side of the automatic preparation apparatus by a housing holder 306. The piston member is arranged to slide vertically by a motor 307 and a drive system 308. The distal end of the cylinder member 304 is formed like a thin needle, and a disposable tip is attached to the distal end. In addition, a discharge needle of compressed air (about 0.3 kg/cm$^2$) is provided in parallel with the disposable tip 309. The tip of the compressed air discharge needle 310 is positioned a little higher than the extreme end of the disposable tip 309.

When the cream 312 in a sampling vessel 311 is sampled by the plunger pump 303, as shown in FIG. 19, the distal end of the disposable tip 309 is put into the inside of an inner lid 313 inside the sampling vessel 311, the distal end of the discharge needle 310 is inserted to be positioned outside the inner lid 313, and the compressed air is discharged from the discharge needle 310. By the compressed air, the inner lid 313 is pressed, so that the cream 312 is injected into the cylinder member 304 through the disposable dip 309.

FIG. 20 composed of FIGS. 20A and 20B is a flowchart showing the flow of steps of the creamy sample automatic injection mode.

At step S40, a disposable housing and a disposable tip 309 are set to the plunger pump 303. At step S41, for example, an empty 50-ml sample container is moved by the robot means 13 from the rack table 301 to the position of an automatic balance 302, and a tare is weighed. The weighing result is output to the microcomputer mentioned earlier. At step S42, a sampling vessel 311 is set by the robot means 13 to the operating position of the plunger pump 303. After the sampling vessel 311 has been moved in parallel displacement to right below the plunger pump 303, as shown in FIG. 9, the sampling vessel 311 is moved upwards so that the distal end of the disposable tip 309 of the plunger pump 303 is inserted into the inside of the inner lid 313 in the sampling vessel 311 and the distal end of the discharge needle 310 is inserted into the outside of the inner lid 313. Then, at step S43, the compressed air is discharged from the discharge needle 310 to cause about 3 g of the cream 312 to be injected into the cylinder member 304. At step S44, the robot means 13 is operated to return the sampling vessel 311 back to the original position.

At step S45, an empty sample container, for which the tare has been weighed, is moved by the robot means 13 to the position of the plunger pump 303, and at step S46, the motor 307 of the plunger pump 303 is actuated to cause the piston member 305 to slide downwards, and a part of the cream 312 (about 1 g) is injected into the empty sample container. At step S47, the robot means 13 is operated to move the sample container holding the cream to the position of the automatic balance 302, and at step S48, the sample is weighed. The result of this weight measurement is also output to the microcomputer mentioned above.

After the disposable tip 309, etc. are discarded at step S49, the weighed sample container is moved by the robot means 13 to the container storage region in the sample row of the turntable 15 at step S50. The extraction solvent injection into the sample container at step S51, the agitation and the dispersion by ultrasonic drive at step S52, the filtration at step S53, and the automatic injection into the input port of the liquid chromatography system are the same as in the mode described earlier, and therefore, description of them is omitted.

In the embodiment described, the rack means is arranged to accommodate only sample containers or sample containers and an automatic balance, but the rack means may be arranged to accommodate various devices according to the purpose of use. For example, the rack means may be arranged to accommodate small-capacity containers, such as filtrate containers, transfer containers and diluted liquid containers in addition to sample containers, and the robot means may be used to change them for those stored on the turntable. The rack means may be arranged so that the containers are changed manually. Or, a conveyer or the like may be used for automatic change of containers disposed in a plane. The rack means, if arranged to circulate in a three-dimensional space, may be capable of automatic change of containers.

The robot means may be formed by various types of robots other than the one described above. It is also possible to provide a plurality of robot means.

Many widely different embodiments of the present invention may be constructed without departing from the spirit and scope of the present invention. It should be understood that the present invention is not limited to the specific embodiments described in the specification, except as defined in the appended claims.

What is claimed is:

1. An automatic preparation apparatus comprising:
    turntable means having a turntable which is provided with a plurality of container receiving portions, and being constructed so as to rotate the turntable in a horizontal plane and to stop a rotated turntable in a desirable position;
    a rack disposed in a stationary position separate from said turntable means, for receiving a plurality of containers;
    a plurality of probe means each comprising a syringe pump and a probe needle connected to the syringe pump through an extendable flexible pipe, for sampling a liquid contained in one of said plurality of containers mounted on the turntable by a predetermined amount of the liquid and for injecting a sampled liquid into the other of said containers on the turntable by the predetermined amount, said probe means having capacities different from one another;

robot means constructed to transfer the containers between said turntable and said rack and to move said probe needles to a desired position on said apparatus;

a pair of chuck members adapted to be attached to said robot means at one ends thereof;

a plurality of first attachments located in a predetermined position of said apparatus, and each constructed to be able to hold the container when chucked by the other ends of said chuck members which have been attached to said robot means, each of said first attachments being formed into a size conformable with that of each container;

a plurality of second attachments located in another predetermined position of said apparatus, and each constructed to be able to hold the probe needle when chucked by the other ends of said chuck members which have been attached to said robot means, each of said second attachments being formed into a size conformable with that of each probe needle; and control means including a microcomputer in which a sequence of desired treatments is programmed, and controlling, according to instructions from the microcomputer, mounting and dismounting operations of said chuck members to and from each of said first attachments, mounting and dismounting operations of said chuck members to and from each of said second attachments, holding and releasing operations of each container by said first attachment which is mounted to said robot means through said chuck members, holding and releasing operations of each probe needle by said second attachment which in mounted to said robot means through said chuck members, transferring operation of a held container, moving operation of a held probe needle to a desired position, sampling operation of the liquid from the container into said probe means, and injecting operation the liquid sampled into said probe means into another container.

2. An automatic preparation apparatus according to claim 1, in which an input port connected to a liquid chromatography system is provided at a fixed position, and a leading end of said probe needle is so constructed an to be insertable into said input port.

3. An automatic preparation apparatus according to claim 1, in which said turntable comprises a heating block for heating the containers and a cooling block for cooling the containers, and said heating and cooling blocks are separated by a partition.

4. An automatic preparation apparatus according to claim 1, in which said robot means comprises a first arm rotatable in a horizontal direction, and a second arm rotatably supported on bearings at a leading end of said first arm so as to be rotatable in the horizontal direction, said robot means being so constructed as to be movable in a vertical direction.

5. An automatic preparation apparatus according to claim 4, in which said pair of chuck members are dismountably attached to a leading and portion of said second arm at one end of each of said chuck members.

6. An automatic preparation apparatus according to claim 5, in which each of said first attachments comprises a pair of members each having at one end portion thereof a hole into which the other end of each of said chuck members is inserted, each of said first attachments being so constructed to hold or release said container when said chuck members are moved in a direction where a distance between said chuck members is extended or shortened.

7. An automatic preparation apparatus according to claim 5, in which each of said second attachments comprises another pair of members each having at one end portion thereof another hole into which the other end of each of said chuck members in inserted, each of said second attachments being so constructed to hold or release said probe needle when said chuck members are moved in a direction where a distance between said chuck members is extended or shortened.

8. An automatic preparation apparatus according to claim 1, in which said liquid is a creamy liquid, and said apparatus further comprises sampling means for sampling a creamy liquid received in one of the containers mounted on said turntable, and for injecting a sampled creamy liquid into the other of the containers on said turntable, and weighing means for weighing said other of said containers prior to receiving the sampled creamy liquid therein, and for weighing said other of said containers after receiving the injected creamy liquid therein, said weighing means being so constructed to output weighing results to said microcomputer.

9. An automatic preparation apparatus according to claim 8, in which said sampling means comprises a cylinder fixed in a predetermined position of said apparatus and having at a leading end thereof a disposable tip, a piston slidably fitted into said cylinder, and a driving portion connected to said piston and electrically connected to said control means so as to move said fitted piston.

* * * * *